United States Patent [19]

Bobo, Jr. et al.

[11] Patent Number: 4,981,467
[45] Date of Patent: Jan. 1, 1991

[54] APPARATUS AND METHOD FOR THE DETECTION OF AIR IN FLUID DELIVERY SYSTEMS

[75] Inventors: Donald E. Bobo, Jr., Orange, Calif.; Alan A. Figler, Crystal Lake, Ill.; Jeffrey L. Frank, Corona, Calif.

[73] Assignee: Baxter International Inc., Deerfield, Ill.

[21] Appl. No.: 485,720

[22] Filed: Feb. 27, 1990

[51] Int. Cl.$^5$ ............................................. A61M 31/00
[52] U.S. Cl. ..................................... 604/65; 604/122; 604/246
[58] Field of Search ............... 604/247, 246, 245, 122, 604/31, 65, 66, 67

[56] References Cited

U.S. PATENT DOCUMENTS 4,673,927  6/1987  Cianciavicchia et al. ........ 604/65 X
4,720,636  1/1988  Benner, Jr. ..................... 604/246 X
4,762,518  8/1988  Kreinick ......................... 604/65 X
4,764,166  8/1988  Spani ............................. 604/65
4,784,643  11/1988  Siretchi et al. .................. 604/122
4,797,655  1/1989  Orndal et al. ................... 604/31 X Primary Examiner—John D. Yasko
Attorney, Agent, or Firm—Gordon Peterson; Debra Dahl-Condino

[57] ABSTRACT

An infusion device includes an infusion pump for delivering a liquid through an infusion conduit from a separate source of the liquid into a patient, a bubble detector for detecting the presence of an air bubble in the infusion conduit, and control circuitry responsive to the bubble detector for determining if the size of the air bubble is unacceptable. The control circuitry is configured to determine if during the time the air bubble is detected it advances a distance indicative of the unacceptable size, one embodiment counting the steps of a linear peristaltic infusion pump for that purpose.

11 Claims, 6 Drawing Sheets

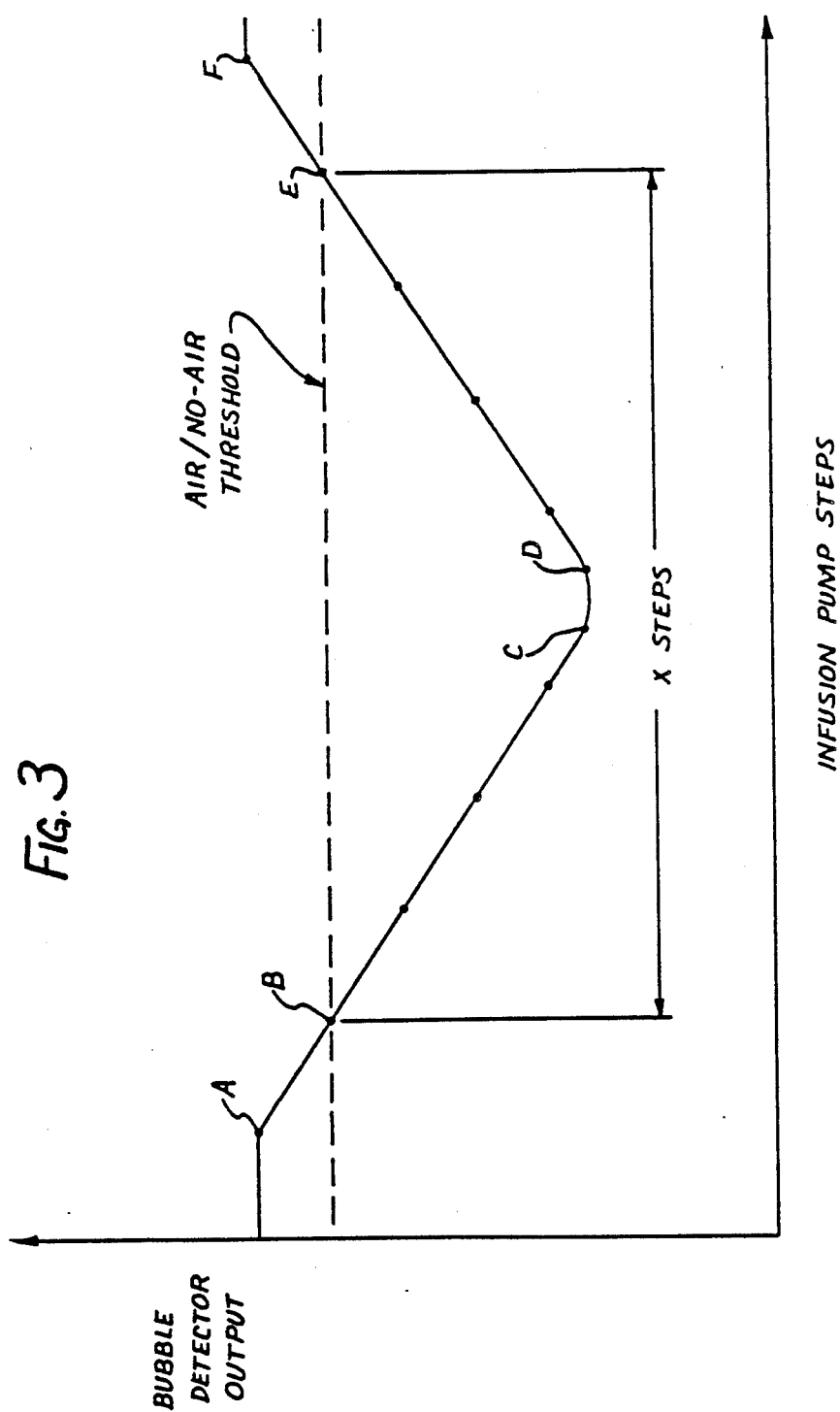

APPARATUS AND METHOD FOR THE DETECTION OF AIR IN FLUID DELIVERY SYSTEMS

BACKGROUND OF THE INVENTION

1. Technical Field

This invention relates generally to medical equipment, and more particularly to a system and methodology for detecting air in a liquid being delivered into a patient.

2. Background Information

An infusion system for delivering a drug or other liquid into a patient often includes an infusion device that operates to deliver the liquid at an adjustable rate or dosage. Commonly housed in a small cabinet suitable for bedside use, the infusion device operates to control the flow of liquid through a flexible tubing or other infusion conduit that extends from an IV bag or other source of the liquid to an IV needle or other cannula inserted in the patient. In addition to a linear peristaltic infusion pump, the infusion device may include microprocessor control circuitry, front panel operator controls, a display, and an alarm, with those things being integrated in a very functional unit designed to improve intravenous drug administration.

In order to guard against air bubbles flowing into the patient, the infusion device may also include an air detector. Sometimes called a bubble detector, it may take the form of an ultrasonic transmitter/receiver pair and related circuitry arranged to sense air bubbles in the infusion conduit. For that purpose, the ultrasonic transmitter and receiver occupy facing positions on opposite sides of the infusion conduit so that ultrasonic energy passes through the infusion conduit in traveling from the transmitter to the receiver. Whenever an air bubble (i.e., a column of air) moves within the infusion conduit to a position between the transmitter and receiver, it causes a recognizable variation in the receiver output (i.e., bubble detector output) and if that variation is sufficient to signify an air bubble of unacceptable size, control circuitry stops the infusion pump and activates the alarm.

Unacceptable air bubble size may differ, however, and so it would be advantageous to have some way to set that value. Then an operator could select a bubble size most appropriate for a particular infusion situation and that would, among other things, avoid the nuisance alarms accompanying too sensitive a setting. But existing infusion devices often use fixed-length bubble detector schemes so that sensitivity is fixed at some predetermined value such as a three-eighths inch bubble length (i.e., about fifty microliters in some commonly used infusion conduit).

One common configuration includes a transmitter and receiver about five-eighths inch long and circuitry configured to pass one-eighth inch long bubbles while stopping three-eighth inch bubbles. The circuitry can recognize variations in bubble detector output from a predetermined threshold value signifying that air between the transmitter and receiver is interrupting 20% of the five-eighths inch bubble detector length (i.e., a one-eighth inch long air bubble), to a predetermined maximum value indicating 60% interruption (i.e., a three-eighths inch long air bubble). When a three-eighths inch long bubble is detected, the control circuitry stops the infusion pump.

So, infusion device sensitivity to air bubble size (i.e., the acceptable air bubble size) is not adjustable. In addition, minimum sensitivity (i.e., maximum acceptable air bubble size) is dependent on the length of the transmitter/receiver pair, a longer transmitter/receiver pair being required to detect longer air bubbles and establish a threshold value much greater than three-eighths inch. But changing the transmitter/receiver pair and associated hardware may be quite costly and inconvenient. So, some other way is needed to reduce infusion device sensitivity in order to pass air bubbles up to an unacceptable size that is larger than the fixed threshold value, and perhaps even larger than the limit imposed by the length of the transmitter/receiver pair.

SUMMARY OF THE INVENTION

This invention solves the problems outlined above by providing an infusion device having control circuitry configured to determine if during the time an air bubble is detected it advances a distance indicative of an unacceptable size. Preferably, that is done with a suitably programmed microprocessor that counts the steps of the infusion pump and compares it with a predetermined value calculated for the particular infusion device and infusion conduit employed. Thus, the infusion device uses a fixed-length bubble detector in a way that can provide reduced sensitivity, and it does so without incurring the cost and inconvenience of modifying the hardware. In addition, the infusion device can be configured to enable operator adjustment of sensitivity level using front panel controls.

Generally, an infusion device constructed according to the invention includes an infusion pump for delivering a liquid through an infusion conduit from a separate source of the liquid into a patient, a bubble detector for detecting the presence of an air bubble in the infusion conduit, and control means responsive to the bubble detector for determining if the size of the air bubble is unacceptable. According to a major aspect of the invention, the control means is configured to determine if during the time the air bubble is detected it advances a distance indicative of the unacceptable size.

Preferably, the control means includes suitably programmed microprocessor circuitry configured to monitor operation of the infusion pump in order to determine the distance the air bubble advances during the time it is detected. In the case of a linear peristaltic infusion pump, for example, the microprocessor counts the steps of the infusion pump as an indication of the distance the air bubble advances and compares it to a value calculated for the particular infusion device and infusion conduit employed. If an unacceptable size is indicated, the microprocessor stops the infusion pump and activates the alarm.

In line with the above, a method of detecting an air bubble of unacceptable size in an infusion conduit through which liquid is to be delivered into a patient includes the step of providing an infusion device having an infusion pump for delivering the liquid through the infusion conduit and a bubble detector arranged to detect the presence of an air bubble in the liquid. The method proceeds by determining if during the time the air bubble is detected it advances a distance indicative of the unacceptable size. Preferably, the step of determining if the air bubble advances a distance indicative of the unacceptable size includes monitoring infusion pump operation, and that may be done with microprocessor circuitry configured to count the steps of a linear peristaltic infusion pump.

BRIEF DESCRIPTION OF THE DRAWINGS

FIG. 3 is a representation of a plot of bubble detector output showing how it may vary as the infusion pump advances the air bubble.

DESCRIPTION OF THE PREFERRED EMBODIMENTS

Figure 1:
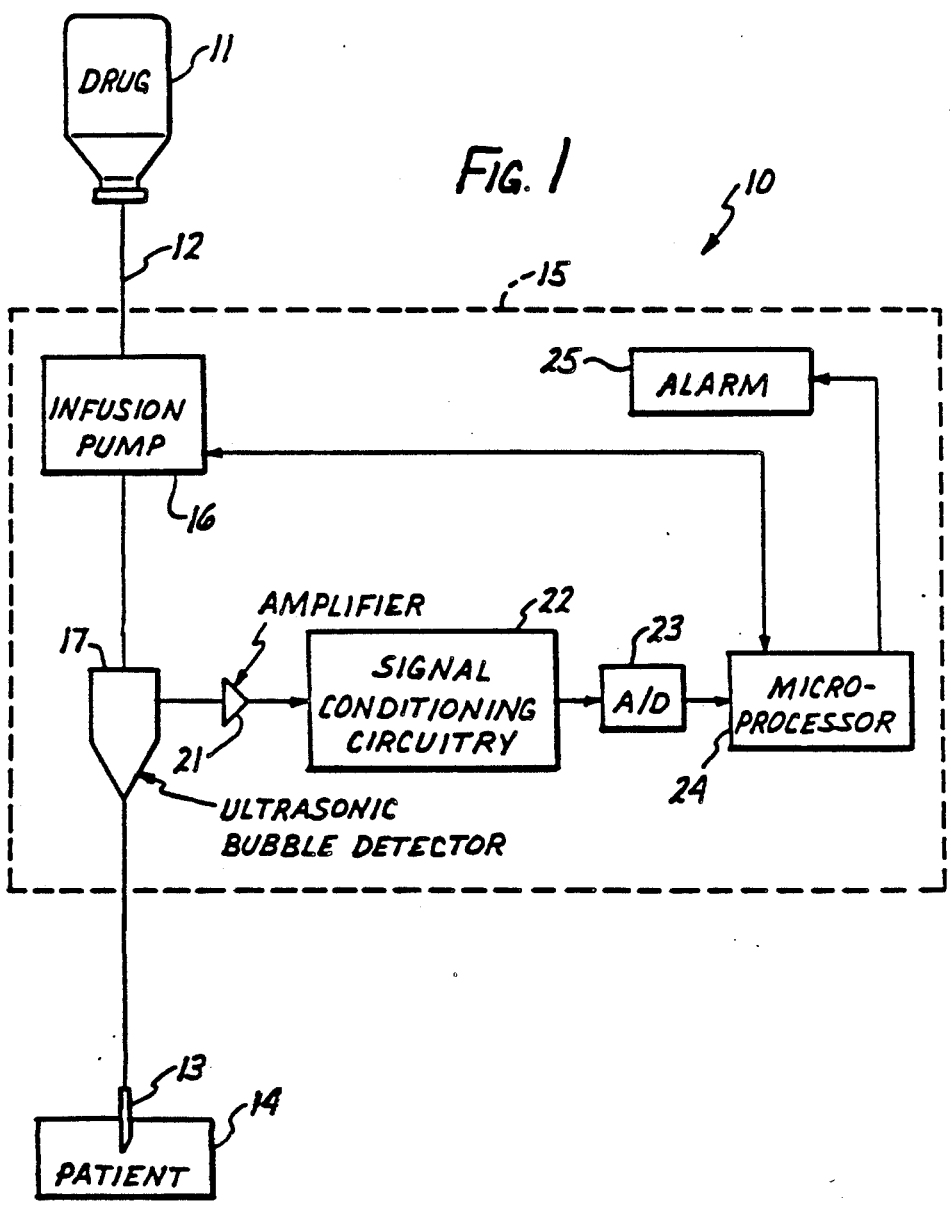
FIG. 1 of the drawings is a diagrammatic representation of an infusion device constructed according to the invention.

FIG. 1 shows an infusion device 10 constructed according to the invention. It operates to deliver a drug or other liquid from a separate source 11 through an infusion conduit 12 to a cannula 13 and into a patient 14. Including some sort of cabinet or other housing depicted in FIG. 1 by the dashed lines 15, the infusion device 10 operates conventionally in many respects and may include many of the features described in U.S. Pat. No. 4,648,869 to Bobo, Jr. That patent is incorporated by reference for the details of construction provided.

An infusion pump 16, preferably a linear peristaltic infusion pump, functions conventionally in many respects as infusion pump means for delivering the liquid through the infusion conduit 12. A bubble detector 17, preferably an ultrasonic bubble detector, functions conventionally in many respects as bubble detector means for detecting the presence of an air bubble in the infusion conduit 12. And a compliment of electronic components, including an amplifier 21, signal conditioning circuitry 22, an analog-to-digital converter 23, and a microprocessor 24, function as control means responsive to the bubble detector means for determining if the size of the air bubble is unacceptable (i.e., assessing bubble size).

Similar to the control circuitry in some existing infusion devices, the control circuitry in the infusion device 10 may be configured to stop the infusion pump 16 and activate an alarm 25 in the event an air bubble of unacceptable size is detected. But unlike existing devices, the control circuitry in the infusion device 10 is configured to monitor the distance an air bubble advances in the infusion conduit 12 as an indication of its size. Preferably, that is done by suitably programming the microprocessor 24 using known programming techniques to perform the steps subsequently described in greater detail.

With the control circuitry so configured, the sensitivity of the infusion device to bubble size (i.e., the unacceptable bubble size threshold) can be set at a selected level. Preferably, that is done with microprocessor programming, and the programming in one embodiment of the invention is so configured that an operator can vary the sensitivity to any of various levels using front panel controls. In addition, the programming is preferably configured to enable the operator to define the sensitivity level in terms of either bubble length (e.g., nine-sixteenths inch) or bubble volume (e.g., seventy-five microliters).

Besides being adjustable, sensitivity is independent of bubble detector size. In other words, the sensitivity of the infusion device 10 (i.e., the unacceptable bubble size threshold) can be set to a greater value than can be done with existing fixed-length bubble detectors, even to a value corresponding to an air bubble longer than the bubble detector. Those things are possible because the control circuitry of the infusion device 10 monitors the distance the air bubble advances in the infusion conduit 12 as the air bubble is causing certain variations in the output of the bubble detector 17. That distance taken in conjunction with the inside diameter of the infusion conduit 12, provides sufficient information for the control circuitry to assess the length of the air bubble (i.e., determine whether the size of the air bubble is unacceptable).

Figure 2:
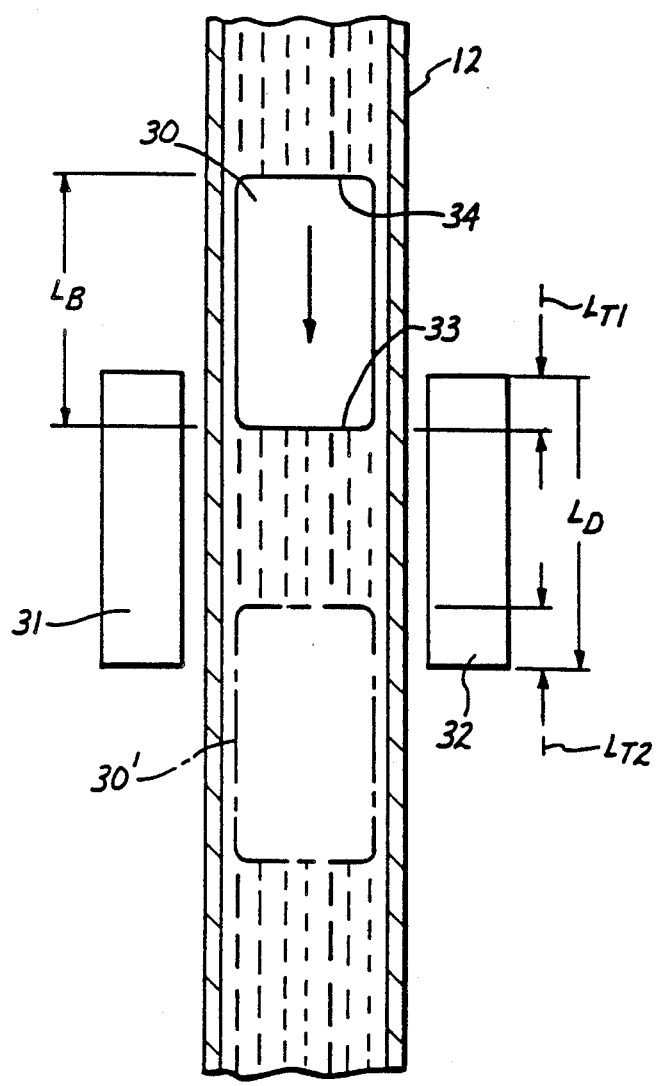
FIG. 2 is a diagrammatic representation showing details of an air bubble advancing within the infusion conduit between the ultrasonic transmitter and receiver of the bubble detector.

FIG. 2 is a diagrammatic representation showing the advance of an air bubble 30 (i.e., a column of air) in the infusion conduit 12. Dimensions are exaggerated for illustrative convenience. The air bubble 30 advances between an ultrasonic transmitter/receiver pair that includes an ultrasonic transmitter 31 and an ultrasonic receiver 32 that are components of the bubble detector 17 shown in FIG. 1. They are arranged in a known way so that ultrasonic energy passes through the infusion conduit 12 in traveling from the transmitter 31 to the receiver 32. As for the air bubble 30, it has a forward end 33, a rearward end 34, and a length ($L_B$) that is the distance between the forward end 33 and the rearward end 34 (FIG. 2). Of course, the air bubble 30 can be something other than air, and so it is intended that the term "air bubble" include a column of any other substance that might be detected by the bubble detector 17.

As the air bubble 30 approaches the transmitter 31 and receiver 32, the forward end 33 eventually passes to a position between the transmitter 31 and receiver 32 where it causes the bubble detector output to vary in some respect, such as amplitude, from an uninterrupted value indicating that there is only liquid between the transmitter 31 and receiver 32 (point A in FIG. 3) to an air/no-air threshold value indicating the initial presence of the forward end 33 of the air bubble 30 (point B). That position can be referred to as a first detectable position, and it is illustrated in FIG. 2 by the position occupied by the forward end 33 of the air bubble 30. It may occur, for example, when the forward end 33 of the air bubble 30 extends one-eighth inch between the transmitter 31 and the receiver 32, as depicted by the dimension in FIG. 2 labelled $L_{T1}$ (the first threshold). That represents an interruption of 20% of the five-eighths inch length of the transmitter 31 and receiver 32 (i.e., the bubble detector length labelled $L_D$ in FIG. 2).

For the air bubble 30 illustrated in FIG. 2, the air bubble length $L_B$ is less than the bubble detector length $L_D$. Thus, as the air bubble 30 continues to advance, the bubble detector output remains constant to point D where the air bubble begins to pass from between the transmitter 31 and the receiver 32. If $L_B$ were equal to or greater than $L_D$, however, the bubble detector output would decrease further to a fully interrupted value less than the value at point C.

At point D in FIG. 3, the bubble detector output begins to increase back to the air/no-air threshold value at point E equal to that at point B. That may be called a second or final detectable position and it is depicted in FIG. 2 by an air bubble 30' in phantom lines. It may occur, for example, when one-eighth inch of the air bubble 30' is still between the transmitter 31 and the receiver 32 as depicted by the dimension in FIG. 2 labelled $L_{T2}$ (the second threshold). Then, as the air bubble 30' passes fully beyond the transmitter 31 and the receiver 32, the bubble detector output increases back to an uninterrupted value at point F equal to that at point A.

Thus, the bubble detector output varies predictably according to the position of the air bubble 30 between the transmitter 31 and the receiver 32 so that monitoring the distance the air bubble advances from the time the bubble detector output varies from point B to point E in FIG. 3, enables the control circuitry to assess air bubble size. According to one aspect of the invention, that distance is monitored by counting the steps of the infusion pump 16. Then, the number of steps to occur (labeled "X" steps in FIG. 3) is compared with a predetermined value indicative of an unacceptable bubble length.

Figure 4A:
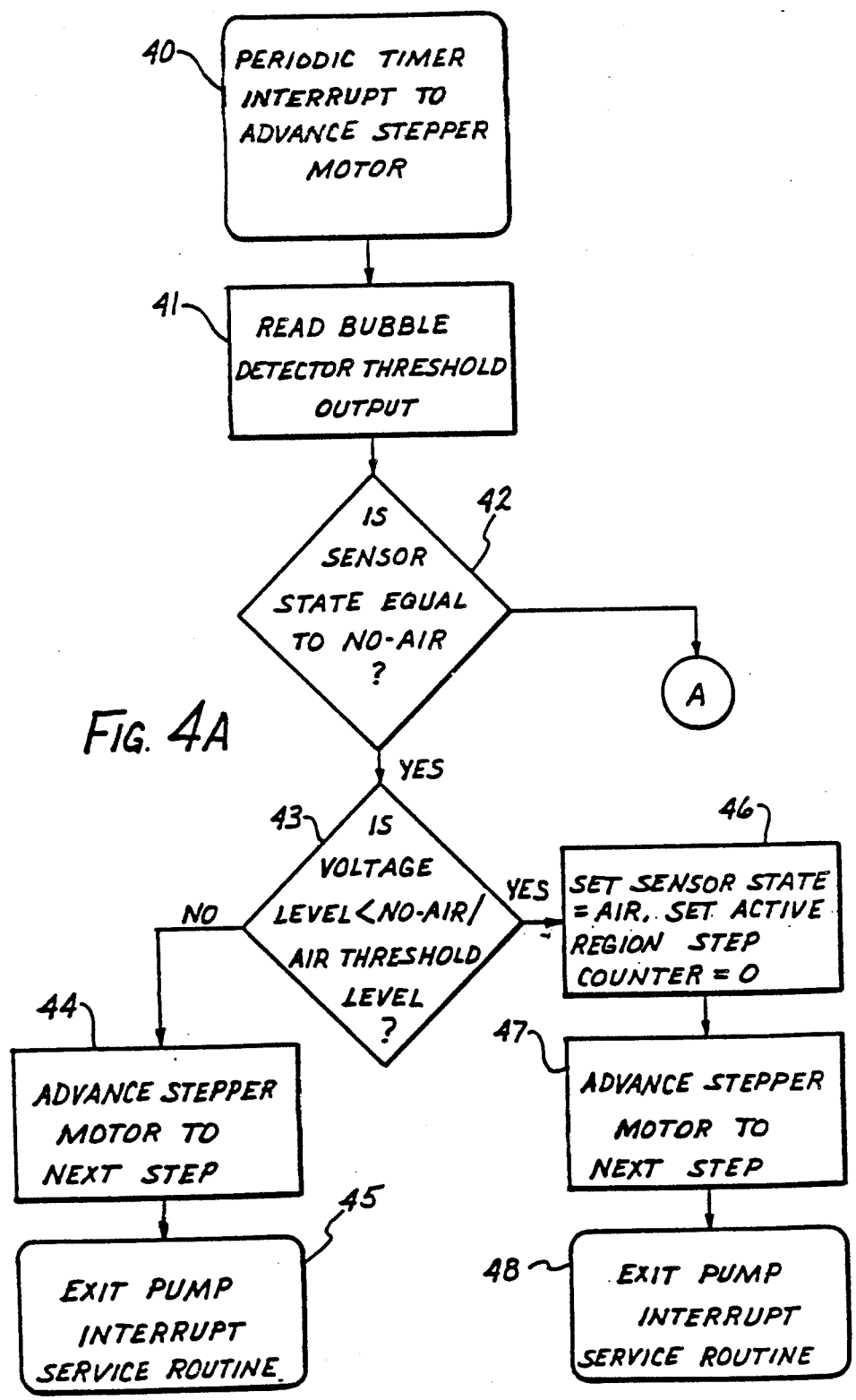
FIGS. 4A–4C combine to form a flow chart showing the methodology employed to assess air bubble size.
Figure 4B:
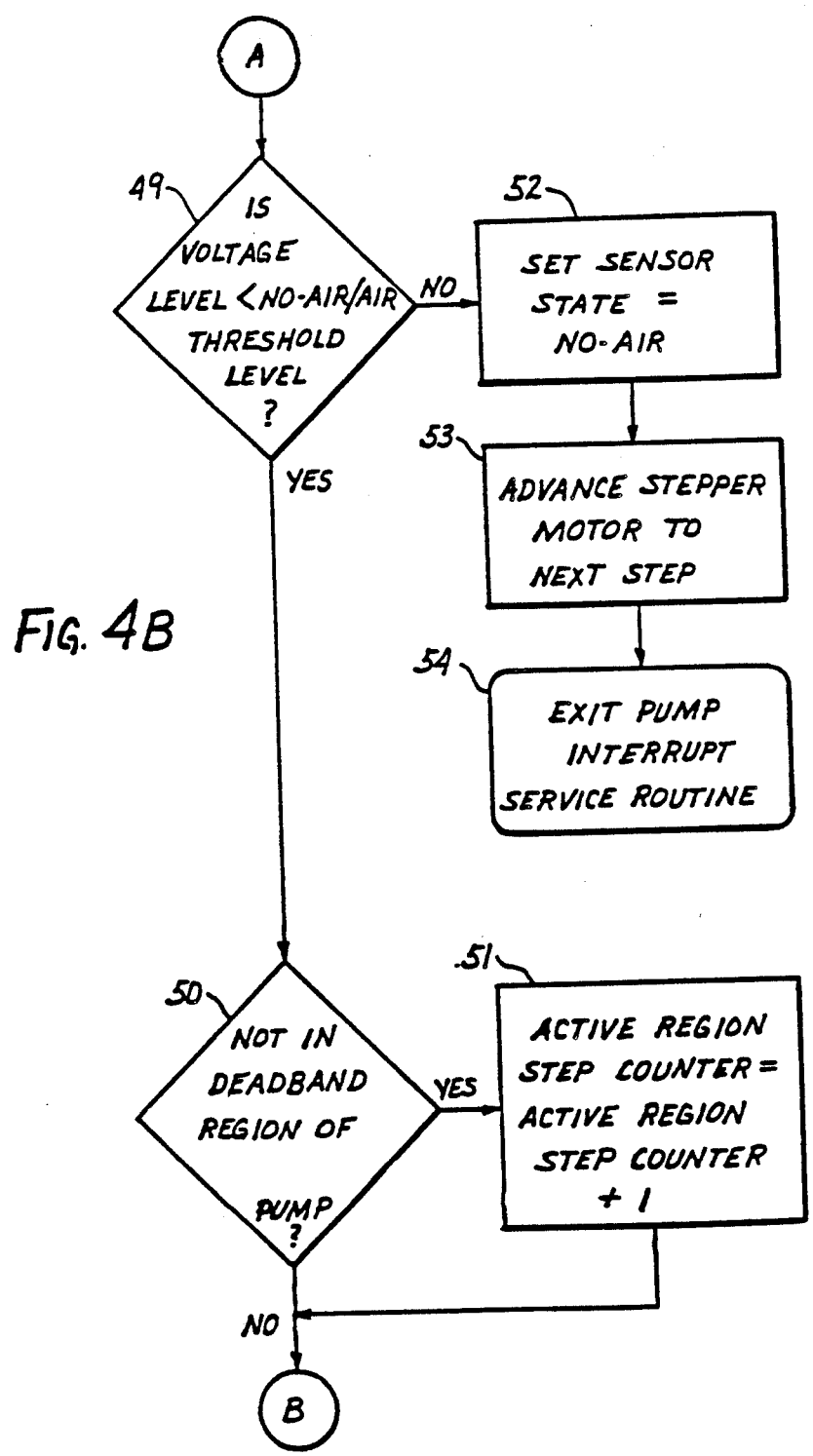
Figure 4C:
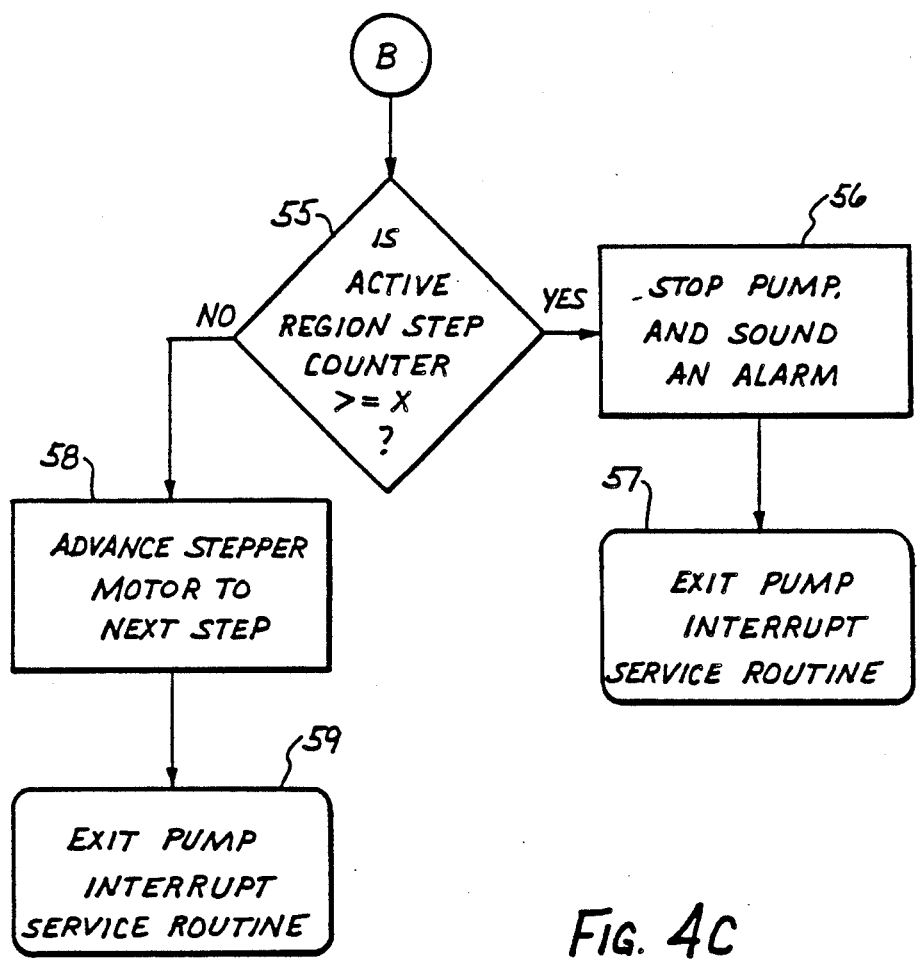

As is apparent from the foregoing and subsequent descriptions, that can be accomplished by suitably programming the microprocessor 24 according to known programming techniques. The flow chart shown in FIGS. 4A–4C provides an example of the steps involved. First, a periodic timer interrupt used to advance the stepper motor of the infusion pump 16 causes program control to proceed to point 40 in FIG. 4A, the start of a pump interrupt service routine. Then the program reads the bubble detector output at 41, examines a SENSOR STATE flag at 42 to determine if it is equal to NO-AIR, and if NO-AIR it is not, the program proceeds to point A in FIG. 4B (subsequently described).

If the SENSOR STATE flag does equal NO-AIR, the program checks at 43 to see if the bubble detector output is less than the air/no-air threshold level. If it is not, the stepper motor is advanced to the next step at 44 and the program exits the pump interrupt service routine at 45. If the bubble detector output is less than the air/no-air threshold level, the program sets the SENSOR STATE flag at 46 to indicate AIR, advances the stepper motor at 47, and exits the pump interrupt service routine at 48.

Considering now FIG. 4B, the program proceeds from point A to see at 49 if the bubble detector output is less than the air/no-air threshold. If it is, the program checks at 50 to see if the infusion pump 16 is not in the deadband region of the peristaltic pump. If NO, program control proceeds to point B in FIG. 4C. If YES, the program first increments an active region step counter at 51 and then proceeds to point B in FIG. 4C.

If the determination at 49 is NO, the program sets the SENSOR STATE flag to equal NO-AIR at 52. Then, it advances the stepper motor to the next step at 53 and exits the pump interrupt service routine 54.

Considering now FIG. 4C, the program proceeds from point B to see at 55 if the active region step counter is equal or greater than X (the predetermined number of steps indicative of an unacceptable bubble size). If YES, the program stops the infusion pump and activates the alarm at 56 and exits the pump interrupt service routine at 57. If NO, the program first advances the stepper motor to the next step at 58 and the exits the pump interrupt service routine at 59.

Thus, by monitoring the distance the air bubble 30 advances in the infusion conduit as the air bubble 30 causes variations in bubble detector output, the control circuitry determines whether the size of the air bubble 30 is unacceptable. Preferably, the control circuitry monitors infusion pump operation for that purpose, counting the strokes or steps of a peristaltic infusion pump. And, preferably, the control circuitry functions are accomplished using known microprocessor programming techniques to perform the steps described.

In order to ensure timely reading of the bubble detector, its state should be read each time the infusion pump is advanced. The bubble detector hardware may still continue to generate a signal indicating air when a nominal three-eighths inch (i.e., fifty microliters) air bubble moves between the transmitter 31 and the receiver 32. However, instead of stopping the infusion pump 16 and activating the alarm 25 as may be done in existing infusion devices, the microprocessor 24 continues to advance the infusion pump 16 while counting the number of advancements from the time bubble detector output first decreased to the air/no-air threshold. Then, the microprocessor continues to infuse the liquid until either the air in the line clears the bubble detector 17 before the air bubble advances "X" steps, where "X" is computed as the number of motor advances indicative of an unacceptable size air bubble, or until the infusion pump 16 advances "X" steps without the air in the line clearing the bubble detector 17. In the second case, the microprocessor stops the infusion pump 16 and activates the alarm 25.

Various attributes of the infusion system may affect the determination of "X." As an example, assume a linear peristaltic pump with the following attributes:

1. A stepper motor controlled pump mechanism with 200 steps per revolution.
2. An eight roller linear peristaltic mechanism with 45-degrees angular travel between the top dead center of adjacent rollers.
3. 144-degrees (80 motor steps) of deadband region during which no net displacement of fluid takes place.
4. 216-degrees (120 motor steps) of active region during which fluid is actively moved through the fluid path.
5. A suitable infusion conduit with precision length and internal diameter (e.g., 100 mils) yielding a volume constant of 1637 steps per milliliter of fluid.
6. Fifty microliters of air equals a bubble length of three-eighths inch, assuming a non-pressurized system.

Then, the volume pumped per stroke (or revolution) is derived as $$\text{Stroke volume} = (200 \text{ steps/rev})/(1637 \text{ steps/ml})$$
$$= 0.122175 \text{ ml/rev}$$

and it follows that the volume pumped per active region step (ARS) is derived as $$\text{Volume/step} = (0.122175 \text{ ml/rev})/(120 \, ARS/\text{rev})$$
$$= 1.0181 \text{ microliter}/ARS$$

The general equation for detecting an "N" microliter air bubble can be derived from the above and expressed in terms of "X" active region steps (ARS). In that regard, material is normally only moved through the infusion conduit during active region steps. That assumes that the infusion system can properly distinguish between motor pulses in the deadband and motor pulses in the active regions. The general equation is $$N \, \mu L = 50 \, \mu L + (X \, ARS)(1.0181 \, \mu L/ARS)$$

Solving for "X" yields a general expression of the number of active region motor steps for a N μL bubble.

$$X\,ARS = (N - 50\ \mu L)/(1.0181\ \mu L/ARS)$$

That value can be set in the programming employed. Alternatively, it can be calculated by the microprocessor to reflect a sensitivity level inputted by an operator of the infusion system. Of course, known error analysis techniques and empirical methods may be employed to account for system parameters that may affect "X."

Thus, the invention provides an infusion device having control circuitry configured to determine if during the time an air bubble is detected the air bubble advances a distance indicative of an unacceptable bubble size. That enables use of a fixed-length bubble detector in a way that can provide reduced sensitivity. In addition, it avoids incurring the cost and inconvenience of modifying the hardware, and the infusion device can be configured to enable operator adjustment of sensitivity level using front panel controls.

We claim:

1. An infusion device, comprising:
   infusion pump means for delivering a liquid through an infusion conduit from a separate source of the liquid into a patient;
   bubble detector means for detecting the presence of an air bubble in the infusion conduit; and
   control means responsive to the bubble detector means for determining if the size of the air bubble is unacceptable;
   which control means is configured to determine if during the time the air bubble is detected it advances a distance indicative of the unacceptable size.

2. An infusion device as recited in claim 1, wherein the control means is configured to monitor operation of the infusion pump in order to determine the distance the air bubble advances during the time it is detected.

3. An infusion device as recited in claim 1, wherein the infusion pump is a linear peristaltic infusion pump and the control means is configured to count the steps of the infusion pump as an indication of the distance the air bubble advances.

4. An infusion device as recited in claim 1, wherein the control means includes microprocessor circuitry.

5. An infusion device as recited in claim 1, wherein the control means is configured to stop the infusion pump if the size of the air bubble is unacceptable.

6. An infusion device as recited in claim 1, wherein the control means is configured to activate an alarm if the size of the air bubble is unacceptable.

7. An infusion device as recited in claim 1, wherein the bubble detector means includes an ultrasonic bubble detector.

8. An infusion device as recited in claim 7, wherein the ultrasonic bubble detector is a fixed-length bubble detector.

9. A method of detecting an air bubble of unacceptable size in an infusion conduit through which liquid is being delivered into a patient, the method comprising:
   providing an infusion device having an infusion pump for delivering the liquid through the infusion conduit and a bubble detector arranged to detect the presence of an air bubble in the infusion conduit;
   determining if during the time the air bubble is detected it advances a distance indicative of the unacceptable size.

10. A method as recited in claim 9, wherein the step of determining if the air bubble advances a distance indicative of the unacceptable size includes monitoring infusion pump operation.

11. A method as recited in claim 9, wherein the step of providing includes providing an infusion device having a linear peristaltic infusion pump and the step of determining if the air bubble advances a distance indicative of the unacceptable size includes counting the steps of the infusion pump.

* * * * *

(12) EX PARTE REEXAMINATION CERTIFICATE (5168th)
United States Patent
Bobo, Jr. et al.

(10) Number: US 4,981,467 C1
(45) Certificate Issued: Aug. 2, 2005

(54) APPARATUS AND METHOD FOR THE DETECTION OF AIR IN FLUID DELIVERY SYSTEMS

(75) Inventors: Donald E. Bobo, Jr., Orange, CA (US); Alan A. Figler, Crystal Lake, IL (US); Jeffrey L. Frank, Corona, CA (US)

(73) Assignee: Baxter International Inc., Deerfield, IL (US)

Reexamination Request:
No. 90/005,857, Nov. 15, 2000

Reexamination Certificate for:
Patent No.: 4,981,467
Issued: Jan. 1, 1991
Appl. No.: 07/485,720
Filed: Feb. 27, 1990

(51) Int. Cl.$^7$ .......................... A61M 31/00; A61M 1/00; A61M 5/00
(52) U.S. Cl. .......................... 604/65; 604/122; 604/246
(58) Field of Search .......................... 604/67, 122–125, 604/153, 245; 128/DIG. 13; 417/1, 63, 477.1; 340/632; 73/19.01

(56) References Cited

U.S. PATENT DOCUMENTS

| | | | |
|---|---|---|---|
| 4,418,565 A | * 12/1983 | St. John | ..................... 73/19.03 |
| 4,496,346 A | 1/1985 | Mosteller | ..................... 604/123 |
| 4,565,500 A | 1/1986 | Jeensalute et al. | ...... 604/123 X |

* cited by examiner

*Primary Examiner*—Michael J Hayes

(57) ABSTRACT

An infusion device includes an infusion pump for delivering a liquid through an infusion conduit from a separate source of the liquid into a patient, a bubble detector for detecting the presence of an air bubble in the infusion conduit, and control circuitry responsive to the bubble detector for determining if the size of the air bubble is unacceptable. The control circuitry is configured to determine if during the time the air bubble is detected it advances a distance indicative of the unacceptable size, one embodiment counting the steps of a linear peristaltic infusion pump for that purpose.

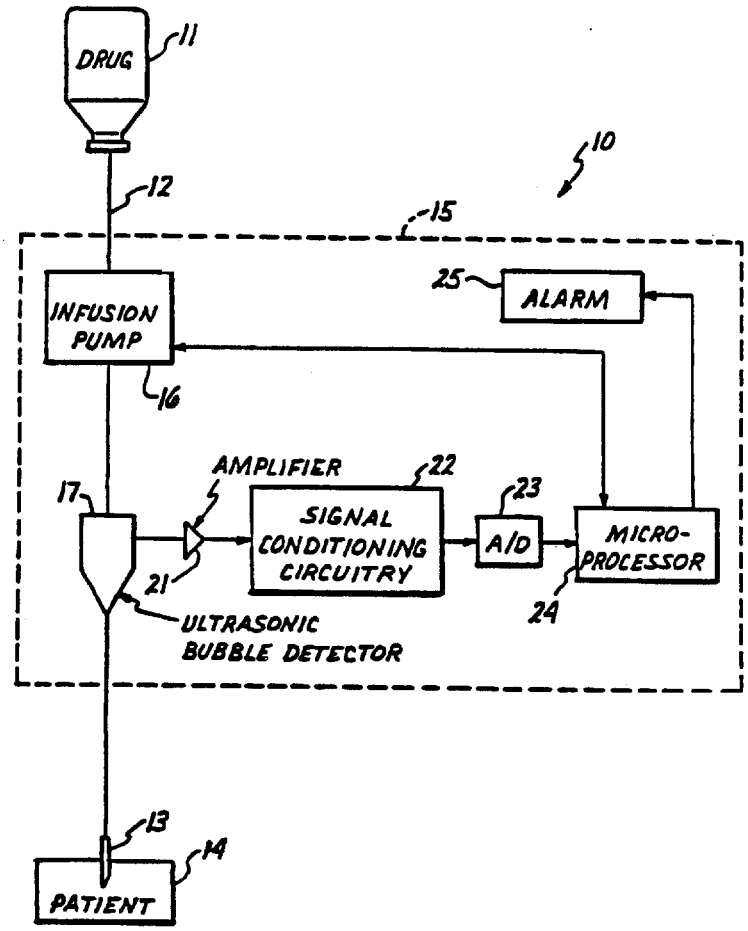

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 9, 10 and 11 are cancelled.

Claim 1 is determined to be patentable as amended.

Claims 2–8, dependent on an amended claim, are determined to be patentable.

New claims 12, 13 and 14 are added and determined to be patentable.

1. An infusion device, comprising:
   infusion pump means for delivering a liquid through an infusion conduit from a separate source of the liquid into a patient;
   bubble detector means for detecting the presence of an air bubble in the infusion conduit; and
   control means responsive to the bubble detector means for determining if the size of the air bubble is unacceptable;
   which *the* control means is configured to determine if during the time the air bubble is detected it advances a distance indicative of the unacceptable size; *and provide a signal if an unacceptable size is indicated,*
   *wherein the control means includes adjustable means for adjustably setting a predetermined detection time value indicative of an unacceptable bubble size threshold and means for comparing the actual detection time value with the threshold value.*

*12. An infusion device, comprising:*
   *an infusion pump means for delivering a liquid through an infusion conduit from a separate source of the liquid into a patient;*
   *an ultrasonic bubble detector for detecting the presence of an air bubble in the infusion conduit; and*
   *control means responsive to the bubble detector means for determining if the size of the air bubble is unacceptable;*
   *which the control means is configured to determine if during the time the air bubble is detected it advances a distance indicative of the unacceptable size.*

*13. An infusion device, comprising:*
   *an infusion pump means for delivering a liquid through an infusion conduit from a separate source of the liquid into a patient;*
   *bubble detector means for detecting the presence of an air bubble in the infusion conduit; and*
   *control means responsive to the bubble detector means for determining if the size of the air bubble is unacceptable;*
   *wherein the control means is configured to determine if during the time the air bubble is detected it advances a distance indicative of the unacceptable size and provide a signal if an unacceptable size is indicated,*
   *wherein the control means includes a predetermined detection time value indicative of an unacceptable bubble size threshold and means for comparing the actual detection time value with the threshold value.*

*14. An infusion device, comprising:*
   *an infusion pump means including a stepper motor for delivering a liquid through an infusion conduit from a separate source of the liquid into a patient;*
   *bubble detector means for detecting the presence of an air bubble in the infusion conduit; and*
   *control means responsive to the bubble detector means for determining if the size of the air bubble is unacceptable;*
   *wherein the control means is configured to determine if during the time the air bubble is detected it advances a distance indicative of the unacceptable size and provide a signal if an unacceptable size is indicated,*
   *wherein the control means includes a step counter for counting the steps of the stepper motor to define an actual detection time value, a predetermined detection time threshold value indicative of an unacceptable bubble size threshold and means for comparing the actual detection time value with the threshold value.*

* * * * *